(12) United States Patent
Kheradpir et al.

(10) Patent No.: US 11,172,992 B2
(45) Date of Patent: Nov. 16, 2021

(54) TRACKED SUCTION TOOL

(71) Applicant: SYNAPTIVE MEDICAL INC., Toronto (CA)

(72) Inventors: Leila Kheradpir, Toronto (CA); Kyle Richard Dupont, Toronto (CA); Jakub Jankowski, Toronto (CA); Samson Ng, Toronto (CA); Kishan Hitesh Shah, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 827 days.

(21) Appl. No.: 15/507,773

(22) PCT Filed: Sep. 26, 2015

(86) PCT No.: PCT/IB2015/057406
§ 371 (c)(1),
(2) Date: Mar. 1, 2017

(87) PCT Pub. No.: WO2017/051224
PCT Pub. Date: Mar. 30, 2017

(65) Prior Publication Data
US 2017/0304009 A1 Oct. 26, 2017

(51) Int. Cl.
*A61B 34/20* (2016.01)
*A61M 1/00* (2006.01)
*A61B 17/00* (2006.01)
*A61B 17/34* (2006.01)
*A61B 90/20* (2016.01)

(52) U.S. Cl.
CPC .......... *A61B 34/20* (2016.02); *A61M 1/7411* (2021.05); *A61M 1/84* (2021.05); *A61B 17/34* (2013.01);
(Continued)

(58) Field of Classification Search
CPC ................ A61M 1/008; A61M 1/0086; A61M 2039/1088; A61M 1/0039;
(Continued)

(56) References Cited

U.S. PATENT DOCUMENTS

| 4,031,896 A | * | 6/1977 | Ronnmark | A61M 1/0047 604/119 |
| 6,021,343 A | * | 2/2000 | Foley | A61B 17/16 600/417 |
| 6,434,507 B1 | * | 8/2002 | Clayton | A61B 17/32002 600/104 |

(Continued)

FOREIGN PATENT DOCUMENTS

| WO | 2014/139018 A1 | 9/2014 | |
| WO | WO2014139018 A1 | * 9/2014 | ............. A61B 19/00 |

OTHER PUBLICATIONS

Day et al. 1993 J. Neurosurg. 78:688-689 (Year: 1993).*
Chen, Tse, "International Preliminary Report on Patentability", PCT Application No. PCT/IB2015/057406 dated Nov. 4, 2016.

*Primary Examiner* — Michael J Tsai
*Assistant Examiner* — Patrick M Mehl

(57) ABSTRACT

A device and method is provided for a trackable suction tool for surgical use. The suction tool provides multiple configurations for the tip and reference tree, while allowing tracking by a navigation system. The tip and reference tree are attached to the suction tool handle by a snap fit, a threaded ring with key and slot connections or semi-Allen key connections, providing specific rotational configurations of the tip, handle and reference tree with each other. The handle may include a rotatable outer sleeve with a tear-shaped orifice for suction regulation and an inner sleeve with a corresponding opening, allowing variable placement of the tear-shaped orifice relative to the longitudinal axis of the suction tool. The features of the device allow a suction tool with multiple configurations to be trackable with a navigation system.

17 Claims, 11 Drawing Sheets

(52) U.S. Cl.
CPC ....... *A61B 90/20* (2016.02); *A61B 2017/0046* (2013.01); *A61B 2017/00681* (2013.01); *A61B 2017/00725* (2013.01); *A61B 2034/207* (2016.02); *A61B 2034/2055* (2016.02)

(58) Field of Classification Search
CPC .... A61B 2017/0046; A61B 2034/2055; A61B 17/34; A61B 2034/207; A61B 2017/00477; A61B 5/05; A61B 5/06; A61B 5/061
See application file for complete search history.

(56) References Cited

U.S. PATENT DOCUMENTS

| | | | | |
|---|---|---|---|---|
| 7,725,162 | B2* | 5/2010 | Malackowski | A61B 34/20 600/424 |
| 2004/0152968 | A1* | 8/2004 | Iversen et al. | A61B 5/05 600/411 |
| 2004/0163501 | A1* | 8/2004 | Chen | B25G 1/066 81/177.1 |
| 2008/0004633 | A1* | 1/2008 | Arata | A61B 34/71 606/130 |
| 2008/0200794 | A1* | 8/2008 | Teichman | A61B 90/39 600/407 |
| 2011/0270081 | A1* | 11/2011 | Burg | A61B 34/20 600/424 |
| 2011/0313281 | A1* | 12/2011 | Grinberg | A61B 17/16 600/424 |
| 2015/0050613 | A1* | 2/2015 | Berkely | A61C 17/0217 433/29 |

* cited by examiner

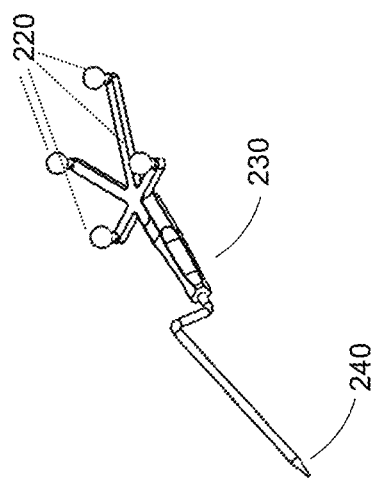
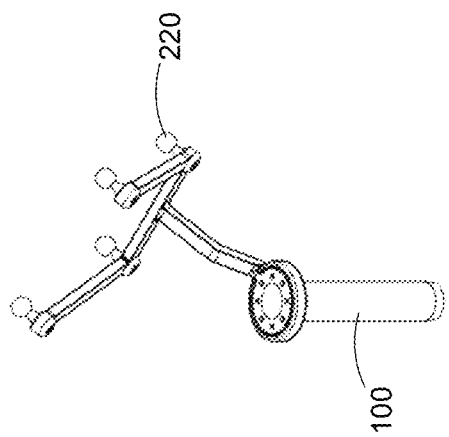
FIG. 2

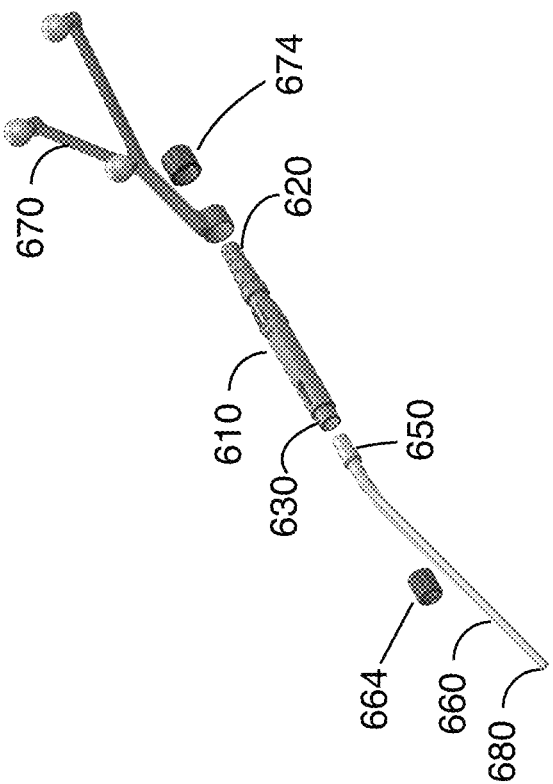
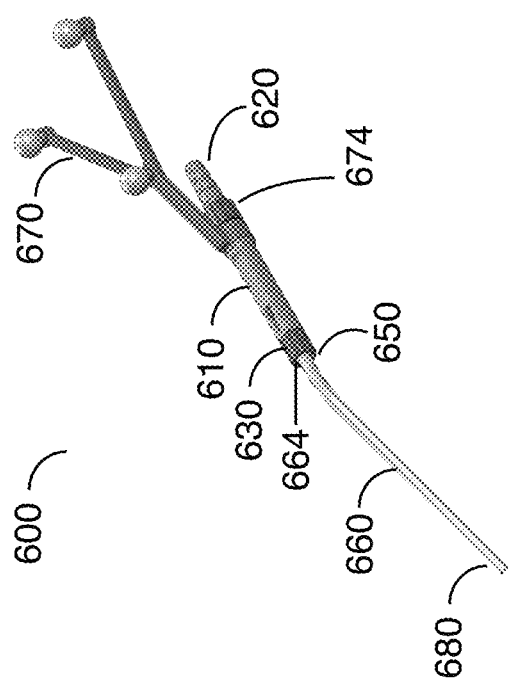
FIG. 6

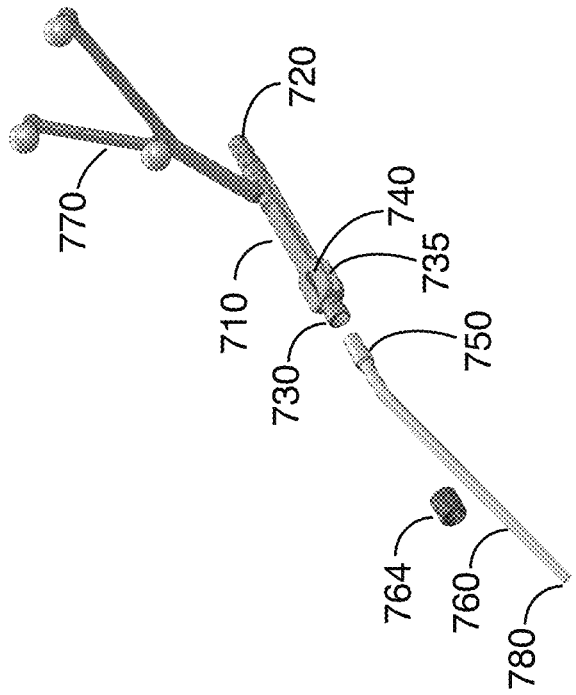
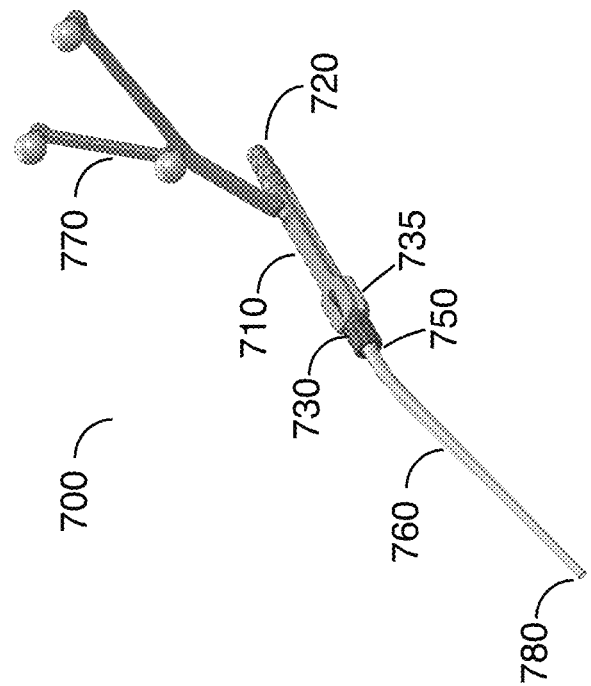
FIG. 7

TRACKED SUCTION TOOL

FIELD

The present disclosure relates to image guided medical procedures using surgical instrument tracking and more specifically to a tracked suction tool.

BACKGROUND

Surgical procedures have been greatly assisted by the implementation of navigation systems. Navigation systems assist in surgery by providing previously acquired imaging information, such as magnetic resonance imaging, during surgery to visualize tissue morphology and locate target areas. Navigation systems may also be used to track surgical instruments and their location within the tissue during surgery, typically incorporating information from previously acquired imaging data.

As an example, minimally invasive brain surgery may incorporate navigation systems to map a target area for surgical resection and access the target area with minimal damage to healthy brain tissue. Corridor-based or port-based surgery is a minimally invasive neurosurgical procedure allowing a surgeon to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

One aspect in minimizing trauma to intact brain matter is to track the location of surgical tools within the tissue by providing the surgical tool with a tracking device. By tracking a surgical tool, its insertion can be guided within the tissue with minimal impact to healthy tissue and the tool can be positioned correctly to serve its purpose. The tool may be tracked by overlaying a map of its position over a previously acquired or real-time imaging of the tissue. Likewise, other navigated procedures, such as spine, ENT (ear nose throat), orthopedic and cardiac procedures benefit from providing surgical tools with a tracking device.

A navigation system typically includes a tracking device or object marker on the surgical tool and a detector to detect the position of the tracking device. In optical navigation systems, object markers can be light emitting diodes (LEDs), reflective stickers, unique structures and patterns or glass spheres, which utilize optical detectors. Alternatively object markers can utilize electromagnetic (EM) or radio frequency (RF) signals, which are detected by antennas. Optical detectors require a line-of-sight between the object marker and detector during operation, but are not subject to noise and distortion from environmental influences that electrical detection and emission systems are subject to.

In some cases, it can be difficult to incorporate a tracking device on a surgical instrument, especially instruments with flexible portions or with multiple configurations. For example, if the tracking device is positioned in a handle or proximal region of the instrument and the distal tip moves or is moved relative to the handle, the distal tip can no longer be accurately tracked. Electromagnetic navigation systems have partly overcome the difficulty of tracking flexible tips and multiple configurations by using a flexible membrane over the tip to connect the distal tracking device with the system on the handle. However, this does not overcome the problem of multiple configurations in which the tip is swiveled about the handle or when the tip is exchangeable.

An important surgical tool is a suction device, which can be used for tissue retention, resection and removal of fluids. A suction device typically includes a handle portion and tip portion. The tip portion can be any one of multiple configurations, such as different lengths, angles and diameters, and may be removable so it can be swapped out to provide the most appropriate configuration for the surgical procedure. Therefore, the multiple configurations of the tip are not amenable to tracking the distal end of the tip through a tracking device on the handle, because the relative positions of the distal end of the tip and handle are different for each configuration. What is lacking in the field is a suction device that can be tracked during surgery while still being amenable to switch between multiple configurations. The present invention attempts to solve this problem to provide a suction device that is trackable over multiple configurations and exchangeable tips.

SUMMARY

An object of the present invention is to provide methods and devices for tracking suction tools using surgical navigation systems.

Thus by one broad aspect of the present invention, a tracked suction device is provided for use in a medical procedure comprising: an elongated tip, having a hollow tubular body, a proximal end and a distal end; an elongated tubular handle, having a central longitudinal passage and means at one end for connection to a vacuum source, reversibly attached to the tip proximal end; a suction regulating orifice in the handle communicating with the central passage; and a tracking mechanism attached to the handle, for tracking the distal end of the tip.

By another broad aspect of the present invention, a method is provided for tracking the position of a tracked suction device in a medical procedure, comprising: registering the tracked suction device with a tracking navigation system; connecting the tracked suction device to a suction mechanism/vacuum source; positioning the tracking markers of the tracked suction device in view of the tracking source (optical camera) of the navigation system to be tracked; and tracking a position of the distal end of the tip of the suction device.

A further understanding of the functional and advantageous aspects of the disclosure can be realized by reference to the following detailed description and drawings.

BRIEF DESCRIPTION OF THE DRAWINGS

FIG. 2 illustrates exemplary tracked instruments with which aspects of the present application may be applied.

FIG. 6 illustrates an alternate embodiment of an assembled and exploded view of a tracked suction device with a tip and tree attached through threaded joint.

FIG. 7 illustrates an alternate embodiment an assembled and exploded view of a tracked suction device with a tip attached through threaded joint with a fixed tree.

DETAILED DESCRIPTION

Figure 1:
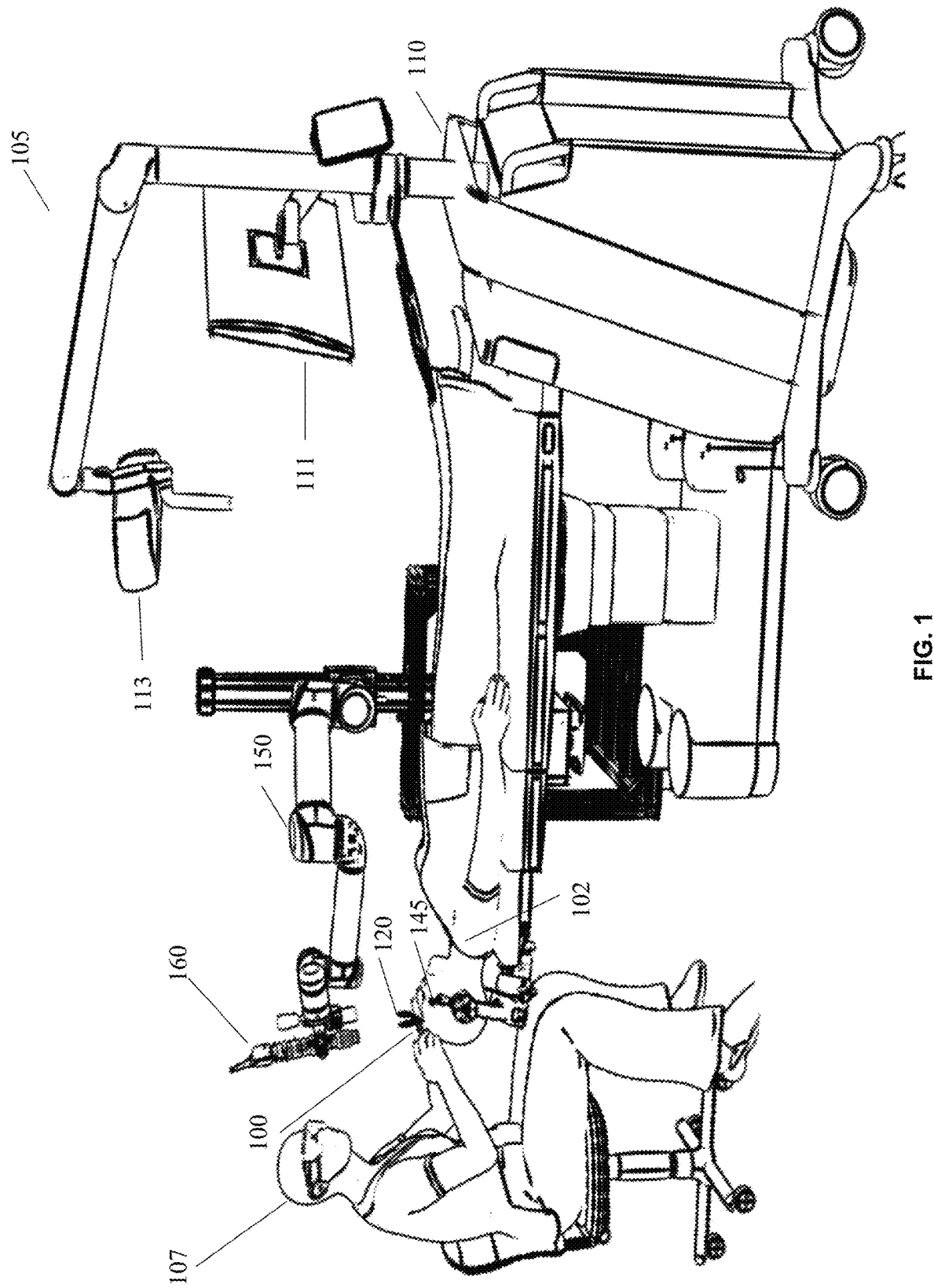
FIG. 1 illustrates systems and equipment of an exemplary neurosurgical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide suction devices that are insertable into a subject or patient for manipulation of internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Several embodiments of the present disclosure seek to address the aforementioned inadequacies of existing devices and methods to support surgical procedures utilizing surgical tools.

Minimally invasive brain surgery using access ports is a recently conceived method of performing surgery on brain tumors previously considered inoperable. One object of the present invention is to provide a system and method to assist in minimally invasive brain surgery. To address intracranial surgical concerns, specific products such as the NICO Brain-Path™ port have been developed for port-based surgery. Referring to FIG. 1 and FIG. 2, port 100 comprises of a cylindrical assembly formed of an outer sheath. Port 100 may accommodate an introducer which is an internal cylinder that slidably engages the internal surface of port 100. The introducer may have a distal end in the form of a conical atraumatic tip to allow for insertion into the sulcal folds of the brain. Port 100 has a sufficient diameter to enable bimanual manipulation of surgical tools within its annular opening such as suctioning devices, scissors, scalpels, and cutting devices as examples.

Surgical Navigation System

The description below makes reference to the brain of patient 102 as an example of tissue to which the techniques herein may be applied. It will be understood, however, that those techniques may also be applied to a wide variety of other tissues. Thus, when the brain of patient 102 is mentioned below, it is simply an example of the various tissues in connection with which the systems and methods herein may be implemented. In particular, suction tools are widely used in surgery, thus a tracked suction device will be useful in virtually all types of navigated procedures. Other examples of navigated procedures wherein a tracked suction device would be useful are spine, ENT (ear nose throat), orthopedic and cardiac surgery.

FIG. 1 illustrates systems and equipment of an exemplary neurosurgical procedure. Referring to FIG. 1, an exemplary navigation system 105 which may be used in surgery is shown. A surgeon 107 conducts a surgery on a patient 102 in an operating room environment. The medical navigation system 105 is illustrated including an equipment tower 110, supporting a computing device (not shown) such as a desktop computer, as well as one or more displays 111 connected to the computing device for displaying images provided by the computing device.

Equipment tower 110 also supports a tracking system 113. Tracking system 113 is generally configured to track the positions of one or more tracking markers 120 mounted on access port 100, any of the above-mentioned surgical tools, or any combination thereof. Such markers, also referred to as fiducial markers, may also be mounted on patient 102, for example at various points on the head 145 of patient 106. Tracking system 113 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 113 to the computing device in equipment tower 110 for subsequent use.

The nature of the markers and the camera are not particularly limited. For example, the camera may be sensitive to infrared (IR) light, and tracking system 113 may include one or more IR emitters (e.g. IR light emitting diodes (LEDs)) to shine IR light on the markers. In other examples, marker recognition in tracking system 113 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 113 can include antennae rather than the above mentioned camera. Combinations of the above may also be employed.

Each tracked object generally includes three or more markers fixed at predefined locations on the object. The predefined locations, as well as the geometry of each tracked object, are configured within tracking system 113, and thus tracking system 113 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 113 is the "Polaris" system available from Northern Digital Inc.

Also shown in FIG. 1 is an automated articulated arm 150, also referred to as a robotic arm or a positioning arm, carrying an external scope 160 (i.e. external to patient 102). External scope 160 may be positioned over access port 100 by robotic arm 150, and may capture images of the brain of patient 102 for presentation on display 111. The movement of robotic arm 150 to place external scope 160 correctly over access port 100 may be guided by tracking system 113 and the computing device in equipment tower 110. The images from external scope 160 presented on display 111 may be overlaid with other images, including images obtained prior to the surgical procedure. The images presented on display 111 may also display virtual models of surgical instruments present in the field of view of tracking system 113 (the positions and orientations of the models having been determined by tracking system 113 from the positions of the markers mentioned above).

Tracking Markers

FIG. 2 illustrates exemplary tracked instruments with which aspects of the present application may be applied. Referring to FIG. 2, active or passive fiduciary markers 220 may be placed on the port 100 and/or any medical instruments 230 to determine the location of these objects using the tracking system 113 and navigation system 105. These markers 220 may be passive reflective spheres configured to be seen by the stereo camera of the tracking system 113 to provide identifiable points for tracking. A tracked instrument in the tracking system is typically defined by a grouping of markers 220, which are used to determine the spatial position and pose of the volume of the tracked instrument in three dimensions. Typically, in known exemplary tracking systems a minimum of three spheres are required on a tracked tool to define the instrument, however it is known in the art that the use of four markers is preferred.

In a preferred embodiment, the navigation system 105 may utilize reflective sphere markers in combination with a stereo camera system, to determine spatial positioning and pose of the medical instruments and other objects within the operating theater. Differentiation of the types of objects and their corresponding virtual geometric volumes may be determined by the specific orientation of the reflective spheres relative to one another giving each virtual object an individual identity within the navigation system 105. This allows the navigation system 105 to identify the medical instrument 230 or other object and its corresponding virtual overlay representation. The location of the markers also provides other useful information to the tracking system 113, such as the object's central point, central axis, orientation, and other information related to the object.

Calibration of Tracked Medical Instrument

It is important that the tracking system 113 know the dimensions of the medical instrument 230 such that, for example, the precise position of the distal end 240 relative to the tracking markers 220 is known. In order to provide the dimensions of the medical instrument 230, the dimensions of the medical instrument may be registered and stored in the navigation system 105, and subsequently calibrated before use in surgery using procedures known in the art. An exemplary calibration procedure is provided below.

Figure 3:
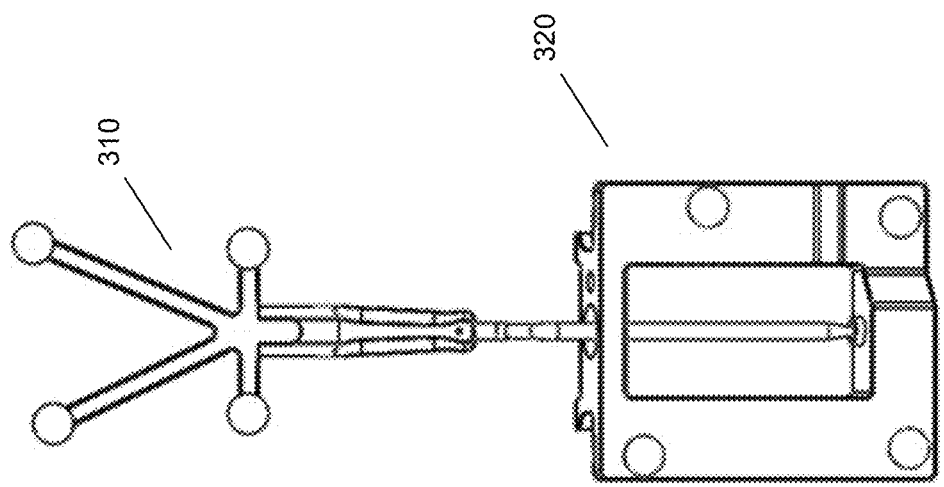
FIG. 3 illustrates a perspective view of a tracked instrument shown in FIG. 2 inserted into a calibration apparatus.

Referring to FIG. 3, a perspective drawing is shown illustrating a tracked instrument 310 inserted into a calibration apparatus 320. The techniques for calibrating a tracked instrument can be found in international application CA2014051004 titled "CALIBRATION APPARATUS FOR A MEDICAL TOOL" which is incorporated by referenced herein in its entirety.

Figure 4:
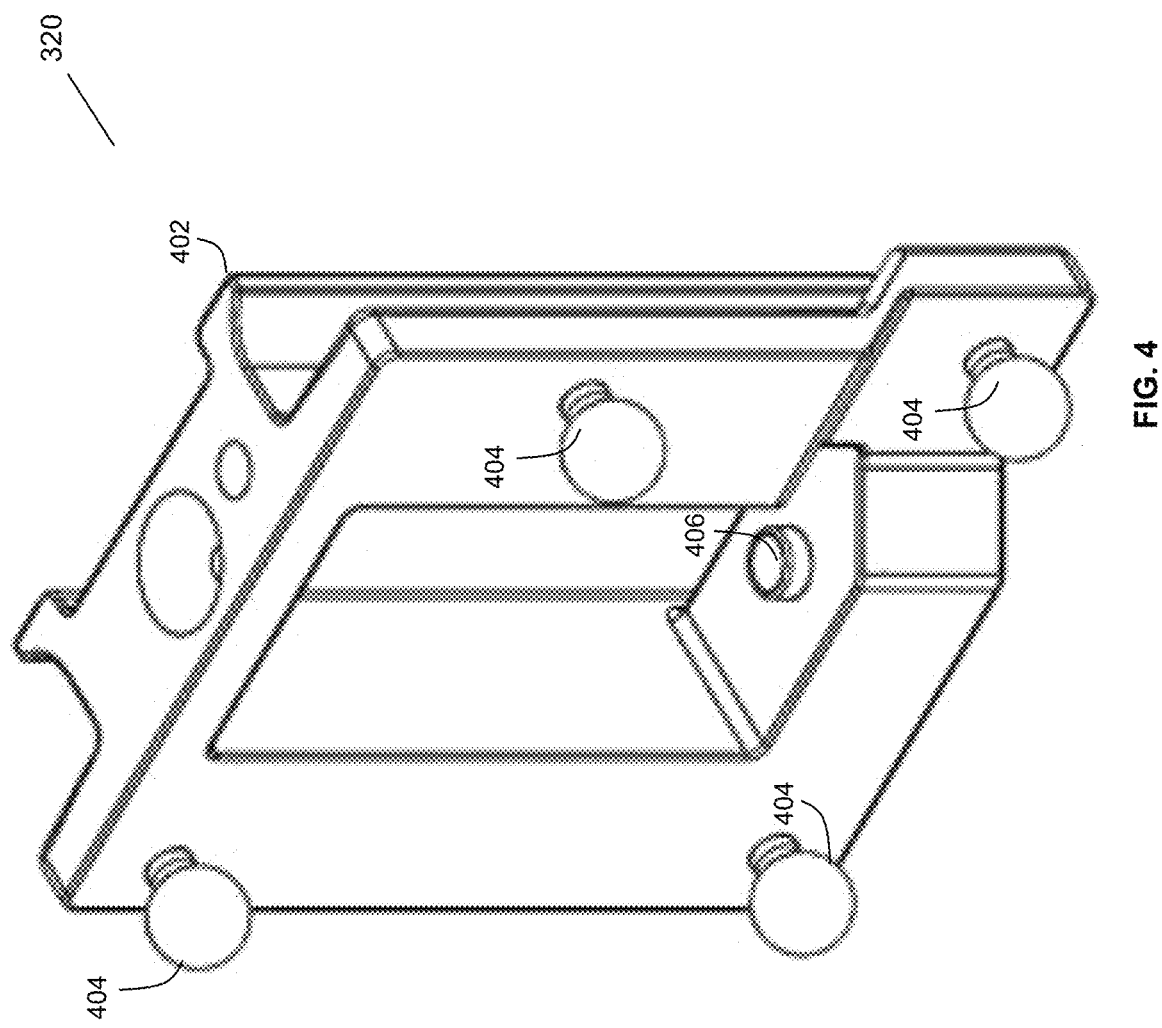
FIG. 4 illustrates a perspective view of a calibration apparatus shown in FIG. 3.

FIG. 4 illustrates a perspective view of a calibration apparatus shown in FIG. 3. Referring to FIG. 4, a perspective drawing is shown illustrating the calibration apparatus 320 in isolation. The calibration apparatus 320 may be used to calibrate a medical tool having a tool tracking marker, such as the medical instrument 230 having the tracking markers 220. The medical tool and the calibration apparatus 320 are typically used in conjunction with a medical navigation system, such as the medical navigation system 105. The calibration apparatus 320 includes a frame 402, at least one frame tracking marker 404 attached to the frame 402, and a reference point 406 formed on the frame 402. In one example, the reference point 406 may be a divot that is of an appropriate shape for securely receiving the distal end 240 of the medical instrument 230. For the purposes of example, the reference point 406 will be referred to throughout as a divot 406. The divot 406 may provide a known spatial reference point relative to the frame tracking markers 404. For example, the medical navigation system 105 may have data saved therein so that the medical navigation system knows the position in space of a floor of the divot 406 relative to the tracking markers 404 to a high degree of accuracy. In one example, a high degree of accuracy may refer to a tolerance of 0.08 mm, but any suitable tolerance may be used according to the design criteria of a particular application.

In the example shown, the calibration apparatus 320 has four passive reflective tracking spheres, but any suitable number of tracking markers 404 may be used and any suitable type of tracking marker 404 may be used according to the design criteria of a particular application, including an active infrared (IR) marker, an active light emitting diode (LED), and a graphical pattern. When passive reflective tracking spheres are used as the tracking makers 404, typically at least three tracking markers 404 will be attached to a same side of the frame 404. Likewise, when a medical instrument 230 having passive reflective tracking spheres is used in conjunction with the calibration apparatus 320, the medical instrument will typically have at least three tracking markers 220 attached thereto.

The distal end 240 of the medical instrument 230 is insertable into the divot 406 to abut against a floor of the divot 406 for validation of the medical instrument 230 dimensions by the medical navigation system 105. Since the medical navigation system 105 knows the precise dimensions of the calibration apparatus 320, the medical navigation system 105 learns the dimensions of the medical instrument 230. In other words, the position of the floor of the divot 406 relative to the tracking markers 404 that the medical navigation system 105 is seeing (e.g., using the camera of the tracking system 113) is known. When the medical instrument 230 is placed in the calibration apparatus 320, as shown in FIG. 3, the position of the distal end 240 of the medical instrument 230 relative to the tracking markers 220 that the medical navigation system 105 is seeing (e.g., using the camera of the tracking system 113) may be learned and saved by the navigation system 105.

Trackable Suction Tool

EXAMPLE 1—REMOVABLE TIP AND TREE

Figure 5:
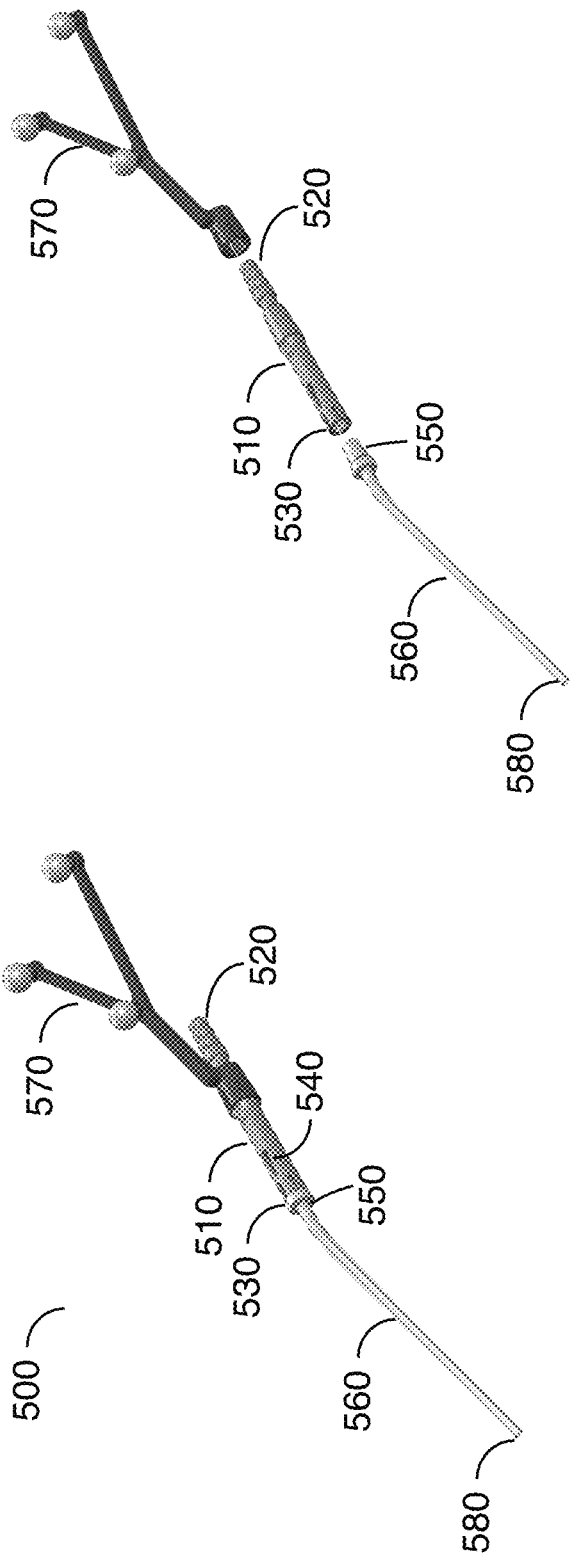
FIG. 5 illustrates an assembled and exploded view of a tracked suction device.

FIG. 5 illustrates an assembled and exploded view of a tracked suction device. Referring to FIG. 5, an example embodiment of a suction tool 500 that may be tracked during surgical procedures is shown. A hollow substantially cylindrical handle 510 has a proximal end 520 and a distal end 530. The handle proximal end 520 is tapered for connection to a suction tube (not shown). The handle includes a tapered elongated slot 540 such as a tear-shaped orifice in the wall of the handle, which is widest at the proximal end and narrowest at the distal end, for controlling the amount of suction provided by the suction tool. The handle distal end 530 is connected to a proximal end 550 of a tubular hollow tip 560. The connection could be, for example, through a snap mechanism as is known in the art. The snap mechanism may include one or more outwardly protruding tabs on the tip proximal end 550 and complementary indentations on the inner surface of the hollow handle distal end 530, thus providing a key and slot method for locking connecting parts in specific rotational angles relative to the central axis. A reference tree 570 is attached to the handle 510 by sliding the reference tree over the handle proximal end 520, where it may also be engaged by a snap mechanism. The handle 510 can be used to hold and manipulate the suction tool 500, such that the tip distal end 580 is directed to the tissue, for example for holding or resecting tissue or suctioning fluids. The tip distal end 580 is also blunted to minimize trauma to tissue while in use. The reference tree 570 provides an optical marker for tracking the position of the suction tool 500 and provides the position information to the tracking system 113. The tip 560 can be removed from the handle 510 by disengaging the snap mechanism. The tip 560 may be one of several different lengths, angles and diameters. Thus, by removing and replacing the tip 560, the suction tool may have different configurations. Information on the parameters for a given tip, such as tip length, diameter and angle, can be entered and stored by the computing device of the navigation system 102, and calibrated using the calibration apparatus 320, so that for each tip 560 used with the suction tool 500, the position of the tip distal end 580 is accurately tracked.

EXAMPLE 2—TIP AND TREE ATTACHED THROUGH THREADED JOINTS

FIG. 6 illustrates an alternate embodiment of an assembled and exploded view of a tracked suction device. The suction device is shown assembled in the left panel and disassembled in the right panel. In this configuration, the trackable suction tool 600 includes a hollow cylindrical handle 610, with a proximal end 620 and a distal end 630. The proximal end 620 is tapered to accommodate connection to a suction tube (not shown). The handle distal end 630 is threaded and is connected to a proximal end 650 of a tubular hollow tip 660, which is also threaded, through a threaded tip tube ring 664. A reference tree 670 is attached to the handle 610 by sliding the reference tree over the handle proximal end 620, and securing it using a threaded tree tube ring 674. As described above, the handle 610 is used to hold and manipulate the suction tool 600, such that the tip distal end 680 is directed to the tissue, and the reference tree 670 provides an optical marker for tracking the position of the suction tool 600, which is recorded by the tracking system 113. The tip 660 can be removed from the handle 610 by rotating the tip tube ring 664 until it is released, and tips of different configurations can thereby be exchanged and used with the suction tool 600. Also as described above, the tip 660 may be one of several different lengths, diameters and angles and by removing and replacing the tip 660, the suction tool 600 may have different configurations.

Information on the parameters for a given tip, such as tip length, diameter and angle, can be entered and stored by the computing device of the navigation system 102, so that for each tip 660 used with the suction tool 600, the position of the tip distal end 680 is accurately tracked. This embodiment further provides for multiple positions of the tip 660 relative to the reference tree 670 around the circumference of the handle 610, allowing easier use for right and left hand users and for different positions of an angled tip without obstructing the line of sight for the reference tree 670. Alternate positions of the tip 660 and tree 670 can be provided, for example, by having complementary nubs and indentations on the tip or tree and the handle 610 to provide a key and slot method for locking connecting parts in specific rotational angles relative to the central axis To accommodate the multiple configurations, information on the parameters for a given tip, such as tip length, diameter and angle, can be entered and stored by the computing device of the navigation system 102, and calibrated using the calibration apparatus 320, so that for each tip 660 used with the suction tool 600, the position of the tip distal end 680 is accurately tracked.

EXAMPLE 3—TIP ATTACHED THROUGH THREADED JOINT WITH FIXED TREE

FIG. 7 illustrates an alternate embodiment an assembled and exploded view of a tracked suction device with the tip attached through threaded joint with a fixed tree. Referring to FIG. 7, another embodiment of a suction tool 700 that may be tracked during surgical procedures is shown. A long tubular handle 710 with a proximal end 720 and a distal end 730 has a flattened portion 735 at its distal end 730 to allow manipulation as for Fukushima design instruments. The flattened portion 735 has a tear-shaped orifice 740 opening to the longitudinal passage of the handle 710, used to control the amount of suction. The handle 710 is connected to a proximal end 750 of a tubular hollow tip 760 using a threaded tip tube ring 764. A reference tree 770 is fixedly attached to the handle 710, for example by welding to the handle or by other methods known in the art. In use, the handle 710 may be used to hold and manipulate the suction tool, such that the distal end 780 of the hollow tip 760 is directed to the tissue, for example for holding or resecting tissue or suctioning fluids. The reference tree 770 provides a tracking marker for tracking the position of the suction tool 700 which is recorded by the tracking system 113. The tip 760 can be removed from the handle 710 by rotating the tip tube ring 764 until the tip is disengaged from the handle. The tip 760 may be one of several different lengths, diameters and angles, thus by removing and replacing the tip, the suction tool 700 may have different configurations. As described above in Example 2, the tip 760 may be rotated about the circumference of the handle 710 to change the relative position of the tip 760 and the reference tree 770. Alternate fixed positions of the tip 760 and reference tree 770 can be provided by complementary nubs and indentations on the tip or tree and the handle 710 thus providing a key and slot method for locking connecting parts in specific rotational angles relative to the central axis. To accommodate the multiple configurations, information on the parameters for a given tip, such as tip length, diameter and angle, can be entered and stored by the computing device of the navigation system 102, and the suction tool 700 can be calibrated using the calibration apparatus 320, so that for each tip 760 used with the suction tool 700, the position of the tip distal end 780 is accurately tracked.

EXAMPLE 4—ROTATABLE TREE

Figure 8:
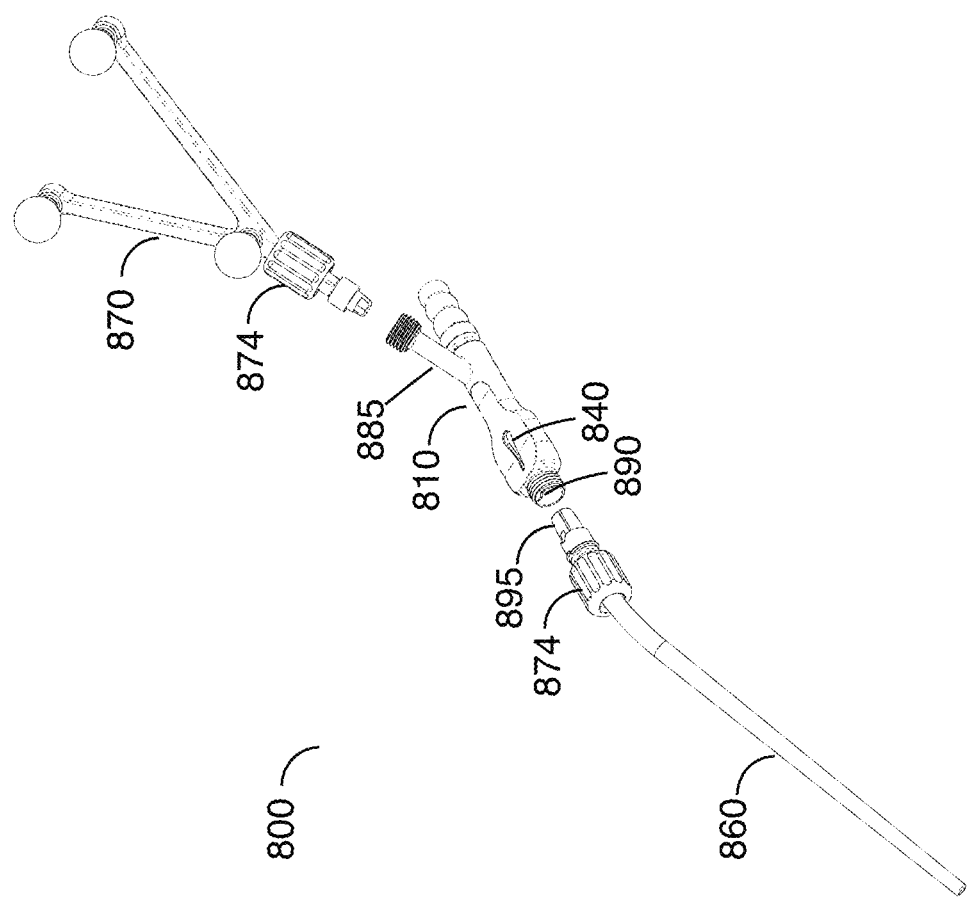
FIG. 8 illustrates an exploded view of a tracked suction device with a rotatable tree.

FIG. 8 illustrates an exploded view of a tracked suction device with a rotatable tree. Referring to FIG. 8, an alternate embodiment of a tracked suction tool 800 is provided. In this embodiment, a handle 810 is connected to a tip 860 and a reference tree 870 through threaded tube rings 874, as described for the tracked suction tool 600 illustrated in FIG. 6. However, in this embodiment of the tracked suction tool 800, the reference tree 870 is connected to the handle 810 through a tubular stem 885 branching from the handle 810. In addition, in this embodiment of the tracked suction tool 800, the inner circumference of the handle threaded joints include a flat surface 890. The tip 860 and reference tree 870 have complementary male semi-Allen joints 895 (i.e., a semi-Allen key or hex joint configuration) that mate with the flat surface 890 of the handle threaded joints, and thereby provide fixed configurations where the flat surface 890 aligns with a semi-Allen joint flat surface 895.

This configuration affords rotation of the reference tree 870 to optimize line of sight and provide a preferred working configuration, while maintaining a fixed rotational axis of the reference tree 870 relative to the elongated slot 840 in the handle 810 used to control suction. This embodiment also allows different reference tree 870 configurations to be switched out for unique identification of one or more suction tools/medical instruments in the same surgical space.

EXAMPLE 5—ROTATABLE HANDLE SLEEVE WITH FIXED TREE

Figure 9:
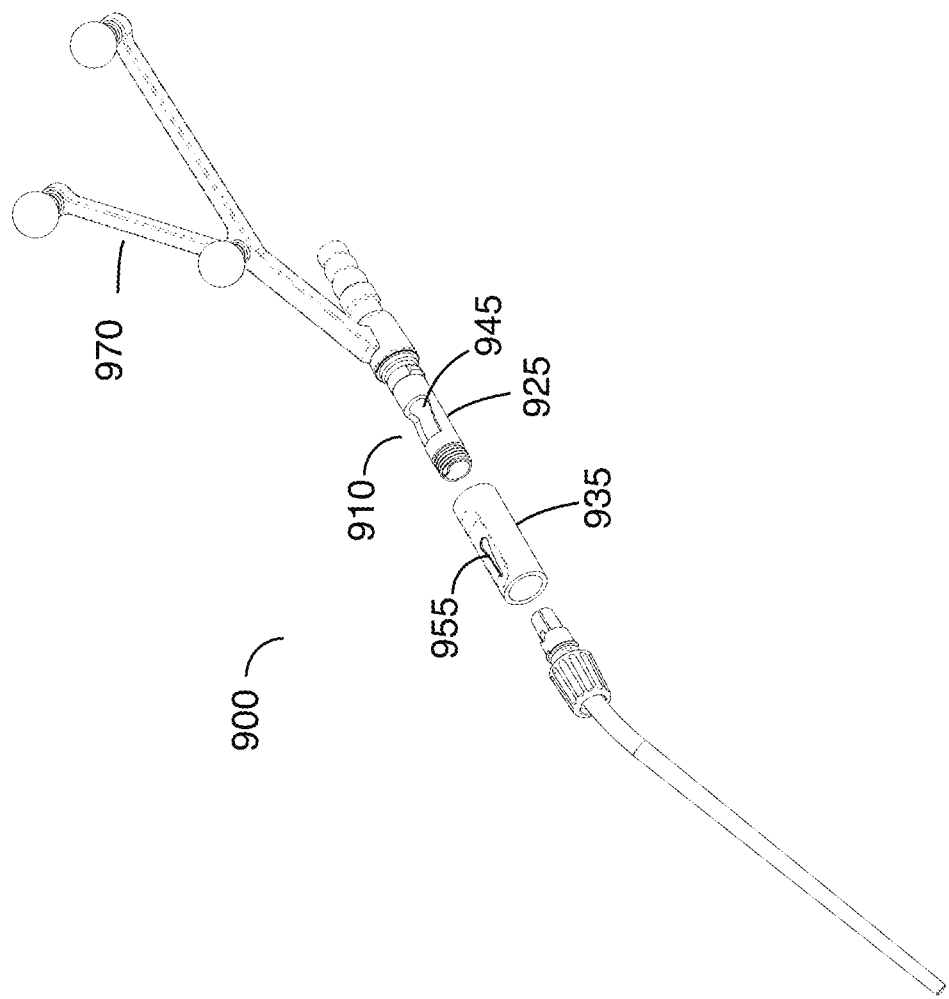
FIG. 9 illustrates a front exploded view of a tracked suction device with a rotatable handle sleeve and a fixed tree.
Figure 10:
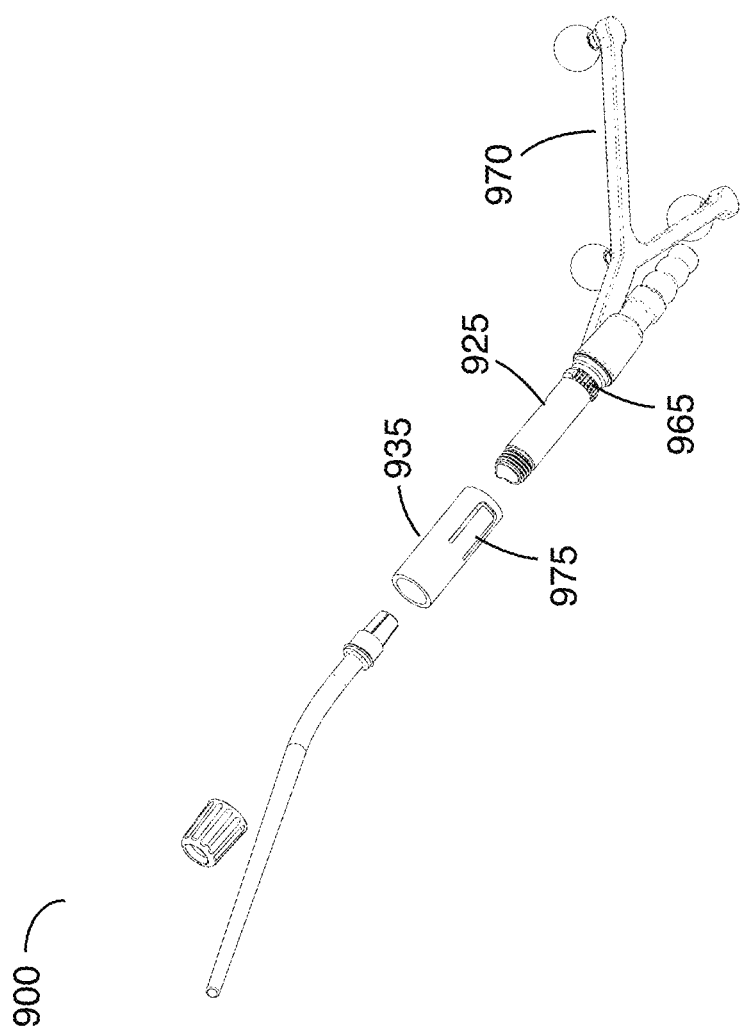
FIG. 10 illustrates an exploded isometric bottom view of the embodiment illustrated in FIG. 9 showing tab and grooves.

Referring to FIG. 9 and FIG. 10, a further embodiment of a tracked suction tool 900 is provided. FIG. 9 illustrates a front exploded view of a tracked suction device with a rotatable handle sleeve and a fixed tree. FIG. 10 illustrates an exploded isometric bottom view of the embodiment illustrated in FIG. 9 showing tab and grooves. This embodiment is as described for the tracked suction tool 700 illustrated in FIG. 7, except the handle 910 comprises an inner sleeve 925 and an outer sleeve 935. The inner sleeve 925 includes a substantially rectangular opening 945 in the handle wall and the outer sleeve 935 includes a tear-drop shaped orifice 955 for regulating the amount of suction provided by the suction tool 900. The outer sleeve 935 can rotate over the inner sleeve, thus providing a changeable orientation of the vacuum orifice 955 around the longitudinal axis of the handle 910 relative to the reference tree 970. Adjustment of the orifice 955 position relative to the reference tree 970 allows a ready adjustment, for example for right-handed versus left-handed use, and switching of hand positions and fingers.

Referring further to FIG. 10, the inner sleeve 925 has grooves 965 around the outer surface and the outer sleeve 935 has a flexible tab 975 with an inwardly facing tongue (not shown) to fit into the inner sleeve grooves 965. Thus the outer sleeve 935 rotates over the inner sleeve 925 and clicks into place at the points where the outer sleeve tongue fits into the inner sleeve grooves 965.

Figure 11:
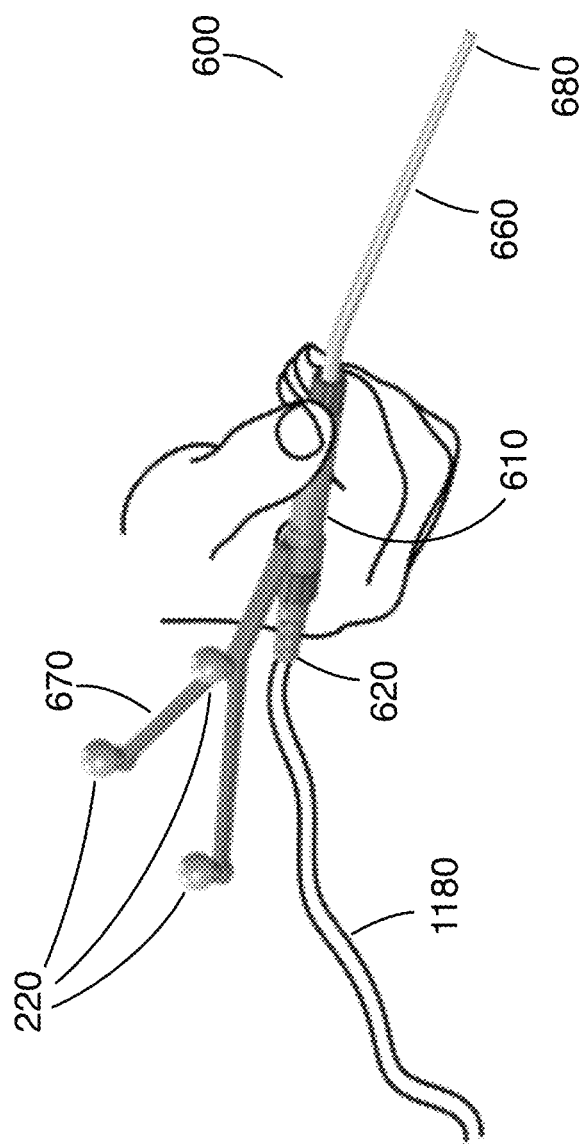
FIG. 11 illustrates a tracked suction tool held in the hand of a user.

FIG. 11 illustrates a tracked suction tool held in the hand of a user. Referring to FIG. 11, a suction tool 600 such as that illustrated in FIG. 6 is held by user (i.e., a surgeon), with the tracking markers 220 of the reference tree 670 providing positional information of the suction tool 600 to the tracking system 113, so the navigation system 102 is able to calculate and display the position of the suction tool tip 660 to the surgeon. Suction tool 600 is connected to suction hose 1180 at the tapered proximal end 620. The tapered aspect of proximal end 620 ensures for a tight and secure fit with suction hose 1180. In the preferred embodiment as illustrated in FIG. 11, suction hose 1180 is located beneath and behind reference tree 670 and handle 610 of suction tool 600, without interfering with the user grasping the tool.

The suction tool 600 is registered in the navigation system 105 and prior to use is calibrated to provide accurate registration of the tracking markers 220 with the tip distal end 680. Calibration ensures that a current configuration of the suction tool 600 is accurately registered in the navigation system 105, including changes such as different tips, adjustment of the reference tree 670, user's grip of the suction tool, and deformations of the tip 660. A vacuum tube 1080 is also shown connected to the proximal end 620 of the handle 610.

As seen in FIGS. 5-11, the suction tool (500, 600, 700, 800, 900) is equipped with a bendable hollow tip (560, 660, 760, 860, 960) wherein the tip includes a bend between the proximal end and distal end. The bend angle may range between 60 and 180 degrees, and preferably 70 to 170 degrees. The bend can be pre-configurable or can be further bent by the user (surgeon) during the medical procedure.

The hollow tip may range in length between 50 mm and 250 mm in length, and preferably between 100 mm and 175 mm. Further, the hollow tip may have a diameter between 3 and 34 FR in diameter, and preferably between 5 FR and 20 FR.

The above embodiments allow a choice of which hand to use to hold the suction tool, specific holding angles to be attained, the reference tree to be manipulated for the best view, and allow suction tools to be customized and replaced with accuracy and minimum inconvenience.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A suction device, the device comprising:
   at least one elongated tip having a hollow tubular body, a tip proximal end, and a tip distal end;
   an elongated tubular handle, having a central longitudinal passage, a handle end, and means for coupling with a vacuum source disposed at the handle end, the handle reversibly coupled with the tip proximal end, the handle having a suction regulating orifice, the orifice communicating with the central longitudinal passage, the orifice comprising a tapered elongated slot for regulating suction, and the tapered elongated slot variably disposable relative to the central longitudinal axis of the handle, whereby suction is regulable; and
   a tracking mechanism coupled with the handle by an attachment mechanism, the tracking mechanism comprising a plurality of reference trees, each reference tree of the plurality of reference trees comprising a rotatable tree, the attachment mechanism configured to rotate a position of the tracking mechanism relative to the handle for tracking the tip distal end, and the rotatable position of the tracking mechanism pre-programmed in a navigation system for providing accurate coordinates of the tip distal end,
   the handle further configured to couple with: each at least one elongated tip by at least one of a threaded nut and a cap, each reference tree of the plurality of reference trees by a tubular stem branching from the handle, and the tip proximal end by the attachment mechanism,
   wherein a line of sight for the navigation system is optimized while maintaining a fixed rotational axis of each reference tree of the plurality of reference trees relative to the tapered elongated slot in the handle,
   wherein each reference tree of the plurality of reference trees comprises a distinct configuration in relation to another reference tree of the plurality of reference trees,
   wherein each reference tree of the plurality of reference trees is switchable to another reference tree of the plurality of reference trees for unique identification of the suction device,
   wherein a position of the orifice is adjustable relative to each reference tree of the plurality of reference trees for facilitating a ready adjustment for right-hand use, left-hand use, switching a hand position, and switching a finger position,
   wherein at least one elongated tip comprises at least one of a distinct length, a distinct diameter and a distinct angle,
   wherein each at least one elongated tip is removable in relation to the handle and interchangeable with another at least one elongated tip,
   wherein the suction device is calibrated by using a calibration apparatus, using the calibration device comprising inserting the suction device into the calibration apparatus, the calibration apparatus comprising a frame comprising a divot having a floor, at least four non-coplanar frame tracking markers frame tracking markers coupled with the frame, and a reference point formed on the frame, the reference point disposed on the floor, and the calibration apparatus configured to securely receive a distal end of the suction device, the reference point having a known spatial position relative to the at least four non-coplanar frame tracking markers, the distal end of the suction device insertable into the divot to abut against the floor for validating dimensions of the suction device by a medical navigation system, the medical navigation system knowing dimensions of the calibration apparatus, and the medical navigation system learning the dimensions of the suction device,
   wherein a position of the tip distal end is trackable for each at least one elongated tip, and
   wherein the medical navigation system saves data relating to the position in space of the floor of the divot relative to the tracking markers, the data comprising a tolerance of 0.08 mm.

2. The device of claim 1,
   wherein the handle comprises: an inner sleeve, the inner sleeve wall having a wall, the wall having an opening; and an outer sleeve rotatable over the inner sleeve, the outer sleeve having the suction regulating orifice, the orifice in the outer sleeve aligning with the opening in the inner sleeve, and the orifice in the outer sleeve rotatable around a longitudinal axis of the handle, and
   wherein the tapered elongated slot comprises a tear shape.

3. The device of claim 1, wherein the at least one elongated tip comprises a bend between the proximal end and the distal end.

4. The device of claim 3, wherein the bend comprises an angular range of approximately 60 degrees to approximately 180 degrees.

5. The device of claim 1, wherein the at least one elongated tip comprises a diameter range of approximately 3 FR to approximately 34 FR.

6. The device of claim 1, wherein the at least one elongated tip comprises a length range of approximately 50 mm to approximately 250 mm.

7. The device of claim 1, wherein the orifice in the handle is disposed in a flattened portion of the handle.

8. The device of claim 1, wherein the attachment mechanism comprises one of a snap attachment and a threaded tube ring.

9. The device of claim 1, further comprising the attachment mechanism, wherein the attachment mechanism comprises a semi-Allen key type female connector and a semi-Allen key type male connector for providing a plurality of fixed rotatable positions.

10. The device of claim 1, wherein the rotatable position of the at least one elongated Lip is pre-programmed in the navigation system for providing accurate position coordinates of the tip distal end.

11. The device of claim 1,
    wherein each at least one reference tree of the plurality of reference trees comprises a plurality of markers, and wherein the navigation system comprises an optical navigation system.

12. The device of claim 11, wherein the plurality of markers comprises at least three optical tracking markers.

13. The device of claim 1, wherein the handle further comprises a tubular stem, and wherein the tracking mechanism is coupled with the handle through the tubular stem and is rotatable around the tubular stem.

14. A method of providing a suction device, the method comprising:
providing at least one elongated tip having a hollow tubular body, a proximal end, and a distal end;
providing an elongated tubular handle, having a central longitudinal passage, a handle end, and means for connection to coupling with a vacuum source disposed at the handle end, the handle reversibly s coupled with the tip proximal end, the handle having a suction regulating orifice, and the orifice communicating with the central longitudinal passage, the orifice comprising a tapered elongated slot for regulating suction, and the tapered elongated slot variably disposable relative to the central longitudinal axis of the handle, whereby suction is regulable; and
providing a tracking mechanism coupled with the handle by an attachment mechanism, providing the tracking mechanism comprising providing a plurality of reference trees, providing the plurality of reference trees comprising providing each reference tree of the plurality of reference trees as a rotatable tree, the attachment mechanism configured to rotate a position of the tracking mechanism relative to the handle for tracking the tip distal end, and the rotatable position of the tracking mechanism pre-programmed in a navigation system for providing accurate coordinates of the tip distal end,
providing the handle further comprising configuring the handle to couple with: each at least one elongated tip by at least one of a threaded nut and a cap, each reference tree of the plurality of reference trees by a tubular stem branching from the handle, and the tip proximal end by the attachment mechanism,
wherein a line of sight for the navigation system is optimized while maintaining a fixed rotational axis of each reference tree of the plurality of reference trees relative to the tapered elongated slot in the handle,
wherein each reference tree of the plurality of reference trees comprises a distinct configuration in relation to another reference tree of the plurality of reference trees,
wherein each reference tree of the plurality of reference trees is switchable to another reference tree of the plurality of reference trees for unique identification the suction device,
wherein a position of the orifice is adjustable relative to each reference tree of the plurality of reference trees for facilitating a ready adjustment for right-hand use, left-hand use, switching a hand position, and switching a finger position,
wherein each at least one elongated tip comprises at least one of a distinct length, a distinct diameter and a distinct angle,
wherein each at least one elongated tip is removable in relation to the handle and interchangeable with another at least one elongated tip,
wherein the suction device is calibrated by using a calibration apparatus, using the calibration device comprising inserting the suction device into the calibration apparatus, the calibration apparatus comprising a frame comprising a divot having a floor, at least four non-coplanar frame tracking markers coupled with the frame, and a reference point formed on the frame, the reference point disposed on the floor, and the calibration apparatus configured to securely receive a distal end of the suction device, the reference point having a known spatial position relative to the at least four non-coplanar frame tracking markers, the distal end of the suction device insertable into the divot to abut against the floor for validating dimensions of the suction device by a medical navigation system, the medical navigation system knowing dimensions of the calibration apparatus, and the medical navigation system learning the dimensions of the suction device,
wherein a position of the tip distal end is trackable for each at least one elongated tip, and
wherein the medical navigation system saves data relating to the position in space of the floor of the divot relative to the tracking markers, the data comprising a tolerance of 0.08 mm.

15. The method of claim 4, further comprising providing the attachment mechanism, wherein providing the attachment mechanism comprises providing a semi-Allen key type female and a semi-Allen key type male connector for providing a plurality of fixed rotatable positions.

16. A method of tracking suction device, the method comprising:
providing the suction device, providing the suction device comprising:
providing at least one elongated tip having a hollow tubular body, a proximal end, and a distal end: providing an elongated tubular handle, having a central longitudinal passage, a handle end, and means for coupling with a vacuum source disposed at the handle end, the handle reversibly coupled with the tip proximal end, the handle having a suction regulating orifice, and the orifice communicating with the central longitudinal passage, the orifice comprising a tapered elongated slot for regulating suction, and the tapered elongated slot variably disposable relative to the central longitudinal axis of the handle, whereby suction is regulable; and
providing a tracking mechanism coupled with the handle by an attachment mechanism, providing the tracking mechanism comprising providing a plurality of reference trees, providing the plurality of reference trees comprising providing each reference tree of the plurality of reference trees as a rotatable tree, the attachment mechanism configured to rotate a position of the tracking mechanism relative to the handle for tracking the tip distal end, and the rotatable position of the tracking mechanism pre-programmed in a navigation system for providing accurate coordinates of the tip distal end,
providing the handle further comprising configuring the handle to couple with: each at least one elongated tip by at least one of a threaded nut and a cap, each reference tree of the plurality of reference trees by a tubular stem branching from the handle, and the tip proximal end by the attachment mechanism,
wherein a line of sight for the navigation system is optimized while maintaining a fixed rotational axis of each reference tree of the plurality of reference trees relative to the tapered elongated slot in the handle,
wherein each reference tree of the plurality of reference trees comprises a distinct configuration in relation to another reference tree of the plurality of reference trees, wherein each reference tree of the plurality of reference trees is switchable to another reference tree of the plurality of reference trees for unique identification of the suction device, wherein a position of the orifice is adjustable relative to each reference tree of the plurality of reference trees for facilitating a ready adjustment for right-hand use, left-hand use, switching a hand position, and switching a finger position, wherein each at least one elongated tip comprises at least one of a distinct length, a distinct diameter and a distinct angle, and wherein each at least one elongated tip is removable in relation to the handle and interchangeable with another at least one elongated tip, rotating the tracking mechanism to a pre-programmed position;

calibrating the suction device by using a calibration apparatus, wherein a position of the tip distal end is trackable for each at least one elongated tip, using the calibration device comprising inserting the suction device into the calibration apparatus, the calibration apparatus comprising a frame comprising a divot having a floor, at least four non-coplanar frame tracking markers coupled with the frame, and a reference point formed on the frame, the reference point disposed on the floor, and the calibration apparatus configured to securely receive a distal end of the suction device, the reference point having a known spatial position relative to the at least four non-coplanar frame tracking markers, the distal end of the suction device insertable into the divot to abut against the floor for validating dimensions of the suction device by a medical navigation system, the medical navigation system knowing dimensions of the calibration apparatus, and the medical navigation system learning the dimensions of the suction device;

registering the suction device and the pre-programmed position of the tracking mechanism with a tracking navigation system;

coupling the suction device with at least one of a suction mechanism and a vacuum source;

positioning a plurality of tracking markers of the suction device in view of a tracking device of the navigation system; and tracking the position of a distal end of the suction device tip, and wherein the medical navigation system saves data relating to the position in space of the floor of the divot relative to the tracking markers, the data comprising a tolerance of 0.08 mm.

17. The method of claim 16, further comprising providing the attachment mechanism, wherein providing the attachment mechanism comprises providing a semi-Allen key type female and a semi-Allen key type male connector for providing a plurality of fixed rotatable positions.

* * * * *